United States Patent
Steinke (10) Patent No.: US 9,786,400 B2
(45) Date of Patent: Oct. 10, 2017

(54) ADJUSTABLE APERTURE DEVICE WITH INTEGRAL APERTURE HOLES

(71) Applicant: Agilent Technologies, Inc., Loveland, CO (US)

(72) Inventor: Armin Steinke, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 887 days.

(21) Appl. No.: 13/683,645

(22) Filed: Nov. 21, 2012

(65) Prior Publication Data

US 2013/0161517 A1    Jun. 27, 2013

(51) Int. Cl.
| | |
|---|---|
| G21K 1/04 | (2006.01) |
| G01J 1/04 | (2006.01) |
| G01J 3/02 | (2006.01) |
| G01J 3/04 | (2006.01) |
| G01N 30/64 | (2006.01) |
| G01N 30/72 | (2006.01) |

(52) U.S. Cl.
CPC .............. *G21K 1/04* (2013.01); *G01J 1/0403* (2013.01); *G01J 1/044* (2013.01); *G01J 1/0437* (2013.01); *G01J 1/0462* (2013.01); *G01J 3/0202* (2013.01); *G01J 3/0229* (2013.01); *G01J 3/0235* (2013.01); *G01J 3/04* (2013.01); *G01N 30/64* (2013.01); *G01N 30/72* (2013.01)

(58) Field of Classification Search
CPC ........................................................ G21K 1/04
USPC ................................. 359/234, 230; 250/373
See application file for complete search history.

(56) References Cited

U.S. PATENT DOCUMENTS

| | | | |
|---|---|---|---|
| 1,746,525 A * | 2/1930 | Darrah .............................. 137/3 |
| 4,403,843 A * | 9/1983 | Maitani et al. ............... 396/110 |
| 4,591,231 A * | 5/1986 | Kaiser et al. ................... 385/73 |
| 6,154,312 A | 11/2000 | Takahama et al. | |
| 6,384,967 B1 | 5/2002 | Watanabe et al. | |

(Continued)

FOREIGN PATENT DOCUMENTS

| | | |
|---|---|---|
| DE | 29604667 U1 | 8/1996 |
| EP | 1577012 A1 | 9/2005 |

OTHER PUBLICATIONS

UK Search Report dated Apr. 23, 2012.
Chinese Office Action dated Mar. 8, 2013.

*Primary Examiner* — David Porta
*Assistant Examiner* — Hugh H Maupin (57) ABSTRACT

An adjustable aperture device for an electromagnetic radiation detecting apparatus includes a position adjustment body configured for adjusting a position of a selected aperture hole of multiple selectable aperture holes, where electromagnetic radiation propagates through the selected aperture hole. The adjustable aperture device further includes a guide unit configured for guiding the position adjustment body along a predefined guide direction, and an aperture body defining the aperture holes and including multiple engagement sections, where the adjustment body is engagable in a selectable one of the engagement sections to thereby select the selected aperture hole. The adjustable aperture device further includes a pre-loading element configured for pre-loading the position adjustment body towards the aperture body, and a drive unit configured for driving the aperture body to move so that the position adjustment body is engaged in a respective one of the plurality of engagement sections.

20 Claims, 3 Drawing Sheets

(56) References Cited

U.S. PATENT DOCUMENTS

| | | |
|---|---|---|
| 7,796,260 B1 * | 9/2010 | Johs et al. .................... 356/369 |
| 2003/0147087 A1 | 8/2003 | Nolte et al. |
| 2004/0061861 A1 | 4/2004 | Rentzsch |
| 2006/0103920 A1 | 5/2006 | Jagemann |
| 2008/0186596 A1 | 8/2008 | Ito |
| 2012/0006998 A1 * | 1/2012 | Kraiczek .................. 250/423 P |
| 2012/0086795 A1 * | 4/2012 | Weiss et al. .................... 348/79 |
| 2013/0124103 A1 * | 5/2013 | Mabie et al. ................... 702/23 |

* cited by examiner

ADJUSTABLE APERTURE DEVICE WITH INTEGRAL APERTURE HOLES

CROSS-REFERENCE TO RELATED APPLICATION

This application claims priority under 35 U.S.C. §119 to United Kingdom Patent Application No. 1122317.9, filed on Dec. 23, 2011, the subject matter of which is hereby incorporated by reference in its entirety.

BACKGROUND

The present invention relates to adjustable aperture devices for an electromagnetic radiation detecting apparatus.

Generally, adjustment of optical elements is known in the art.

US 2006/0103920 discloses a device, such as a rotary disk or a longitudinal slider, for retaining optical components, this device comprising apertures arranged next to one another, and a raceway having detents being provided in the direction of the arranged apertures, which detents are embodied in such a way that they are to be brought into click-stop engagement with a spherical body running along the raceway, in order to hold the device in a selected position. In order to enable gentle click-stopping of the spherical body with a wide capture region, it is proposed that the detents have, in the running direction, a profile comprising a combination of two arc-shaped profiles, such that an outer profile of lesser curvature surrounds an inner profile of greater curvature.

DE 296 04 667 discloses a changer device for optical elements.

In liquid chromatography, a fluidic analyte may be pumped through conduits and a column comprising a material which is capable of separating different components of the fluidic analyte. Such a material, so-called beads which may comprise silica gel, may be filled into a column tube which may be connected to other elements (like a control unit, containers including sample and/or buffers) by conduits. When a fluidic sample is pumped through the column tube, it is separated into different fractions. The separated fluid may be pumped in a flow cell in which the different components are identified on the basis of an optical detection mechanism.

In such an optical detection mechanism, ultraviolet radiation is guided along the flow cell. In such an optical system, inter alia an aperture device is required having an aperture hole which needs to be positioned precisely relative to an optical path and which needs to be adjustable regarding aperture hole dimension. In this kind of optical measurement devices such as spectrometers with the product names (Starlight or ORCA) there is the requirement to switch slit apertures in a reproducible way.

Conventionally, this is done by a micromechanical member which comprises a silicon structure in which both the required aperture slits as well as a precise adjustment provision for the individual aperture slits is foreseen in the form of solid state hinges integrated in a silicon substrate. Although such a member works properly, it is expensive in manufacture. Conventional aperture devices for detection cells may hence suffer from a high complexity.

SUMMARY

It is an object of the invention to provide an adjustable aperture device which can be manufactured with reasonable effort.

According to an exemplary embodiment of the present invention, an adjustable aperture device for an electromagnetic radiation detecting apparatus is provided, wherein the aperture device comprises a position adjustment body configured for adjusting a position of a selected aperture hole of a plurality of selectable aperture holes, wherein electromagnetic radiation is to propagate through the selected aperture hole, a guide unit configured for guiding the position adjustment body along a predefined guide direction, an aperture body having, as an integral part thereof or integrally formed therein, the plurality of aperture holes and comprising a plurality of engagement sections, wherein the position adjustment body is engagable in a selectable one of the plurality of engagement sections to thereby select the selected aperture hole from the plurality of selectable aperture holes, a pre-loading element configured for pre-loading (or pre-stressing or biasing) the position adjustment body towards the aperture body, and a drive unit configured for driving the aperture body to move so that the position adjustment body is engaged in a respective one of the plurality of engagement sections.

According to another exemplary embodiment, an electromagnetic radiation detecting apparatus for detecting electromagnetic radiation carrying information indicative of components of a fluidic sample separated by a sample separation system is provided, the electromagnetic radiation detecting apparatus comprising an electromagnetic radiation source configured for generating primary electromagnetic radiation and for directing the primary electromagnetic radiation onto the separated fluidic sample, an electromagnetic radiation detector configured for detecting secondary electromagnetic radiation resulting from an interaction of the components of the fluidic sample with the primary electromagnetic radiation, and an adjustable aperture device having the above mentioned features and being arranged in an electromagnetic radiation path between the electromagnetic radiation source and the electromagnetic radiation detector.

According to still another exemplary embodiment, a sample separation system for separating components of a fluidic sample is provided, the sample separation system comprising a mobile phase drive configured for driving a mobile phase through the sample separation system, a separation element configured for separating the components of the fluidic sample in the mobile phase, and an electromagnetic radiation detecting apparatus having the above mentioned features for detecting electromagnetic radiation carrying information indicative of the components of the fluidic sample.

According to yet another exemplary embodiment, a method of adjusting a position of a selected aperture hole of a plurality of selectable aperture holes of an adjustable aperture device having the above mentioned features is provided, wherein the method comprises driving the aperture body by the drive unit to move so that the position adjustment body is engaged in a respective one of the plurality of engagement sections.

The term "aperture body having, as an integral part thereof, the plurality of aperture holes" may particularly denote that the aperture holes are directly formed as through holes in the aperture body, i.e. are not substitutably mounted or separable from the aperture body. In contrast to this, the aperture holes form part of the aperture body.

The term "electromagnetic radiation" may particularly denote an ensemble of photons. The electromagnetic radiation may be, for instance, in the range of visible light, ultraviolet radiation, or infrared radiation. Primary electromagnetic radiation irradiated onto the fluidic sample and secondary electromagnetic radiation received from the fluidic sample in response to the primary electromagnetic radiation may or may not differ regarding wavelengths. Such primary electromagnetic radiation and such secondary electromagnetic radiation may be monochromatic or polychromatic.

According to an exemplary embodiment of the invention, a highly precise positioning arrangement for entering one of a plurality of available aperture holes into an optical path is provided. In this context, position adjustment may be performed by a mechanically biased position adjustment body which is pushed against an edge of an aperture body which has, integrated in itself, the individual aperture holes. The position adjustment body may be temporarily locked in one of a number of engagement sections located along this edge, wherein each engagement section corresponds to an assigned one of the aperture holes to be brought in alignment with the optical beam path. In other words, when the position adjustment body is locked in one of the engagement sections, this corresponds to the selection of one of the aperture holes to be presently active. The high accuracy of the position adjustment is obtained on the one hand by a cooperating shape of the position adjustment body and the engagement sections and on the other hand by a predictable, reproducible and well-defined guiding performance which guides the position adjustment body so that it can only move along a precisely defined direction. Since the direction of the position adjustment body is always well-defined and since the arrangement of the engagement sections is strictly correlated to the arrangement of aperture holes, the precision in control of the position adjustment body translates into a precise positioning of the selected aperture hole. Particularly, the accuracy of embodiments of the invention results from a functional decoupling of the driving of the aperture body by a drive unit (such as a stepper motor) from the positioning performed by the rigidly guided position adjustment body. Furthermore, by integrally forming the aperture holes as part of the aperture body, any misalignment between aperture holes and aperture body is eliminated. When, in contrast to this, aperture hole members are provided separately from an aperture body effects such as clearance or the like of such substitutable aperture hole members may occur which deteriorates positional accuracy.

In the following, further exemplary embodiments of the adjustable aperture device will be explained. However, these embodiments also apply to the electromagnetic radiation detecting apparatus, the sample separation system, and the method.

In an embodiment, the position adjustment body is a sphere or a ball. Due to the rotational symmetry of a sphere, the position adjustment by the sphere is always achieved independently of its orientation.

In another embodiment, the position adjustment body comprises a cylinder with a cone or ball-tip or any orbiform. For instance, a cylinder may be biased and guided so as to move only along a cylindrical symmetry axis.

In an embodiment, the guide unit is configured for guiding the position adjustment body via exactly two contact points. Contacting the position adjustment body at exactly two contact points by a guide unit allows to precisely define the degrees of freedom according to which the position adjustment body is allowed to move. On the other hand, the system is not over defined when guiding the position adjustment body via two contact points.

In an embodiment, the guide unit is configured as a prismatic structure, a pair of parallel guide pins or a guide pin in combination with a guide plate. When the position adjustment body is mounted with defined limitations regarding movability by using one of the given guiding structures, a high spatial accuracy may be achieved. Particularly, two parallel aligned guide pins having a curved surface on which the sphere (as an example of the position adjustment body) contacts the guide pins has turned out as a specifically simple and reliable guiding system.

In an embodiment, the pre-loading element is configured as a spring, such as a helical spring. However, other kinds of springs are possible such as a leaf spring, a flat spring or the like. The spring may be configured so that a pushing force is applied to the position adjustment body which pushes the position adjustment body with a predefined pre-loading force against the edge of the aperture body which edge has the engagement sections.

In another embodiment, the pre-loading element is configured as a magnetic force generation system, an electrostatic force generation system or an elastic rod. For example, a magnetic force may be generated by one or more magnetic elements (such as one or more permanent magnets and/or one or more electromagnet such as a current-carrying coil). In such an embodiment, it is advantageous, that also the position adjustment body is made of magnetic material such as a ferromagnetic material (for instance from iron, nickel or cobalt). An elastic rod may for instance be a rubber rod which has elastic abilities, for instance can be compressed in a default state so as to press the position adjustment body within an elastic back driving force towards the engagement sections of the aperture body. In other exemplary embodiments also other kinds of forces may be used for designing the pre-loading element such as an electrostatic force or gravitational force.

In an embodiment, the plurality of aperture holes in the aperture body are of different sizes and/or different shapes. For instance, it may be necessary to adapt an area of a presently used or active aperture hole to the presently available intensity of the electromagnetic radiation. A larger aperture hole results in a high intensity and therefore in a proper signal-to-noise ratio. On the other hand, the depth of focus of the optical mapping is better for smaller aperture holes. Therefore, a selection between several available aperture holes of the aperture body can be made. Additionally or alternatively, the plurality of aperture holes in the aperture body may be of different shapes. This allows to adapt the optical mapping properties as well.

In an embodiment, the aperture body is configured to be rotatable by the drive unit to thereby engage the position adjustment body in indentations formed between adjacent teeth distributed along a circumference of the aperture body as the plurality of engagement sections. In such an embodiment, the aperture body may be a flat cylinder or a disk which is configured to rotate around its symmetry axis. Along a part of an edge of the aperture body, the engagement sections may be formed as indentations, for instance curved regions between adjacent teeth. The position adjustment body may then be locked between adjacent teeth to be brought into a mechanically stable configuration.

In an embodiment, the aperture body is configured to be linearly translatable by the drive unit to thereby engage the position adjustment body between adjacent teeth aligned along an edge of the aperture body as the plurality of engagement sections. In such an alternative embodiment, an edge of a, for instance plate-shaped, aperture body may be provided with the sequence of teeth and indentations. The position adjustment body may then be locked again between two adjacent teeth. Such an aperture body may be shifted in a reciprocating manner by a stepper motor or the like.

In an embodiment, the aperture device comprises a gear mechanism configured for transferring drive energy from the drive unit to the aperture body. Such a gear mechanism may comprise a chain wheel drive, a belt drive or any other mechanical mechanism for transmitting mechanical energy provided by the drive unit to move the aperture body for selection of an engagement section into which the position adjustment body locks, whereby also a desired aperture hole is selected.

In an embodiment, the gear mechanism comprises a first toothed gear wheel mounted on the drive unit and a second toothed gear wheel cooperating engagingly with the first toothed gear wheel, wherein the second toothed gear wheel has a camshaft configured for engaging with energy transfer engagement sections arranged along a circumference of the aperture body. Therefore, the gear mechanism may comprise a toothed gear wheel configuration, i.e. cooperating disk-shaped members each having a sequence of circumferentially distributed teeth which engage into one another so as to rotate cooperating toothed gear wheels together. A camshaft may be considered as a shaft to which a cam is fastened. The camshaft can be used to operate the aperture body by power provided by the drive unit. For instance, the camshaft may be configured with two opposing protrusions which can engage energy transfer engagement sections aligned along a part of the circumference of the aperture body.

In an embodiment, the camshaft is configured for being decoupled from the aperture body upon completion of an adjustment procedure of the aperture device. Upon rotation of the camshaft, the camshaft freewheels over slightly less than 180° until a new engagement with an energy transfer engagement section occurs. Each engagement event relates to a switching from one selected aperture hole to another one, while allowing for a temporary decoupling between camshaft and aperture body in the freewheeling intervals. Thus, the camshaft does not disturb the spatial positioning between two position adjustment switches of the system.

In an embodiment, a position adjustment performed by the position adjustment body, the guide unit and the pre-loading element is functionally decoupled from, particularly is independent of, a driving of the aperture body performed by the drive unit. Therefore, the accuracy of the positioning is independent of the performance of the drive unit. For instance, temperature effects or aging effects acting on the drive unit and resulting in a modified drive behavior do not negatively influence the position accuracy, since the latter is defined by the cooperation of position adjustment body, guide unit and pre-loading element which are spatially, structurally and functionally independent of an operation of the drive unit. In other words, the drive unit only operates as an energy supply unit, wherein position adjustment is not influenced by the drive unit.

In an embodiment, all (or part of) the components of the aperture device are made of materials having thermal expansion coefficients which differ for the different materials by less than about 10%. For example, a support of the aperture device may be made of aluminum, whereas the aperture body may be made of a plastic material such as polyamide with 40% carbon. Upon adjusting the carbon component of the plastic material of the aperture body, the thermal expansion coefficient of the aperture body and of the support may be adjusted to one another so that the positioning accuracy is not negatively influenced by a temperature change.

In an embodiment, the plurality of engagement sections are configured as prismatic grooves formed between correspondingly shaped protrusions along an edge of the aperture body. In other words, the grooves may have the shape of a prism. This shape ensures a contact along two contact points, thus prevents an overdefinition of the guiding performance and guarantees an accurate positioning.

In an embodiment, the pre-loading element is configured for applying a pre-loading force to the position adjustment body along a pre-loading force direction (for instance a spring axis) which is inclined by a predefined angle relative to a guide direction along which the guide unit (defined by parallel guide pins) exclusively enables motion of the position adjustment body. For instance, this inclination angle may be in a range between 30° and 60°. This simplifies the spatial arrangement of pre-loading element, aperture position body and guide unit relative to one another. These components have to be arranged in close relationship but without undesired interaction. The described angular arrangement meets both conditions at the same time.

In an embodiment, the pre-loading element and the guide unit are configured for applying a guided pre-loading force to the position adjustment body for forcing the position adjustment body to apply an abutting force oriented towards a rotation axis of the aperture body. Particularly, the force impact via the ball to the wheel may be performed so that the ball is pressed in a defined way against the wheel in direction of the wheel's rotation axis. Thus, the ball is always oriented in a certain position or at a certain point which results in a precise positional reproducibility.

In the following, further exemplary embodiments of the electromagnetic radiation detecting apparatus will be explained. However, these embodiments also apply to the adjustable aperture device, the sample separation system, and the method.

In an embodiment, the electromagnetic radiation source is configured as one of the group consisting of a deuterium lamp, a xenon lamp, and a tungsten lamp. In an embodiment, the electromagnetic radiation detector comprises one of an optical light detector, and an ultraviolet radiation detector. In an embodiment, the electromagnetic radiation detector comprises one of a single detection element, a linear array of detection elements, and a two-dimensional array of detection elements. In an embodiment, the electromagnetic radiation detecting apparatus comprises a grating between the adjustable aperture device and the electromagnetic radiation detector. In an embodiment, the electromagnetic radiation detecting apparatus comprises an off-axis mirror between the electromagnetic radiation source and the adjustable aperture device.

In an embodiment, the electromagnetic radiation detecting apparatus comprises a flow cell through which the fluidic sample flows and which is arranged between the electromagnetic radiation source and the adjustable aperture device. In the context of this application, the term "flow cell" may particularly denote a fluidic member having a fluidic channel delimited by a tubing through which a fluidic sample, which may already be separated, is conducted. Electromagnetic radiation may be emitted into the flow cell, and subsequently the fluidic sample may be characterized by detecting the absorption of the electromagnetic radiation by the fluidic sample, or by detecting fluorescence radiation emitted by the fluidic sample upon being excited with primary electromagnetic radiation.

In the following, further exemplary embodiments of the sample separation system will be explained. However, these embodiments also apply to the adjustable aperture device, the electromagnetic radiation detecting apparatus, and the method.

The sample separation system may comprise a separation element filled with a separating material. Such a separating material which may also be denoted as a stationary phase may be any material which allows an adjustable degree of interaction with a fluidic sample so as to be capable of separating different components of such a fluidic sample. The separation element may be arranged in a fluidic path upstream the detector so that fractions of a sample separated by the separation element may be subsequently detected by the detector device.

The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the separation element may be filled with a fluid separating material, wherein the fluid separating material may comprise beads having a size in the range of essentially 1 µm to essentially 50 µm. Thus, these beads may be small particles which may be filled inside the separation section of the microsample separation system. The beads may have pores having a size in the range of essentially 0.01 µm to essentially 0.2 µm. The fluidic sample may be passed through the pores, wherein an interaction may occur between the fluidic sample and the pores.

The sample separation system may be configured as a fluid separation system for separating components of the sample. When a mobile phase including a fluidic sample passes through the sample separation system, for instance with a high pressure, the interaction between a filling of the column and the fluidic sample may allow for separating different components of the sample, as performed in a liquid chromatography device.

However, the sample separation system may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass through the column. Due to the different interaction of the different protein fractions with the filling of the column (for instance using a liquid chromatography device), the different samples may be distinguished, and one sample or band of material may be selectively isolated as a purified sample. The detector may then serve for controlling the success of the purification.

The sample separation system may be configured to conduct the mobile phase through the system with a high pressure, for instance of 50 bar to 100 bar, particularly of at least 600 bar, more particularly of at least 150 bar.

The sample separation system may be configured as a microsample separation system. The term "microsample separation system" may particularly denote a sample separation system as described herein which allows to convey fluid through microchannels having a dimension in the order of magnitude of less than 500 µm, particularly less than 50 µm, more particularly less than 100 µm or less than 50 µm or less.

Exemplary embodiments may be embodied based on most conventionally available HPLC systems, such as the Agilent 150 Series Rapid Resolution LC system or the Agilent 1100 HPLC series (both provided by the applicant Agilent Technologies—see www.aqilent.com—which shall be incorporated herein by reference).

The separating device preferably comprises a chromatographic column providing the stationary phase. The column might be a glass or steel tube (for example with a diameter from 50 µm to 5 mm and a length of 1 cm to 1 m) or a microfluidic column (as disclosed for example in EP 1577012 or the Agilent 150 Series HPLC-Chip/MS System, which is commercially available from Agilent Technologies, Santa Clara, Calif. USA). For example, a slurry can be prepared with a powder of the stationary phase and then poured and pressed into the column. The individual components are retained by the stationary phase differently and separate from each other while they are propagating at different speeds through the column with the eluent. At the end of the column they elute one at a time. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface, though in EBA a fluidized bed is used.

The mobile phase (or eluent) can be either a pure solvent or a mixture of different solvents. It can be chosen for example to minimize the retention of the compounds of interest and/or the amount of mobile phase to run the chromatography. The mobile phase can also been chosen so that the different compounds can be separated effectively. The mobile phase may comprise an organic solvent like for example methanol or acetonitrile, often diluted with water. For gradient operation water and organic is delivered in separate bottles, from which the gradient pump delivers a programmed blend to the system. Other commonly used solvents may be isopropanol, tetrahydrofuran (THF), hexane, ethanol and/or any combination thereof or any combination of these with aforementioned solvents.

The fluidic sample may comprise any type of process liquid, natural sample like juice, body fluids like plasma or it may be the result of a reaction like from a fermentation broth.

The HPLC system may comprise a sampling unit for introducing the fluidic sample into the mobile phase stream, a detector for detecting separated compounds of the fluidic sample, a fractionating unit for outputting separated compounds of the fluidic sample, or any combination thereof.

BRIEF DESCRIPTION OF DRAWINGS

Various objects and attendant advantages of representative embodiments will be readily appreciated and become better understood by reference to the following detailed description of embodiments in connection with the accompanying drawings. Features that are substantially or functionally equal or similar will be referred to by the same reference signs.

The illustrations in the drawings are schematic.

DETAILED DESCRIPTION

Figure 1:
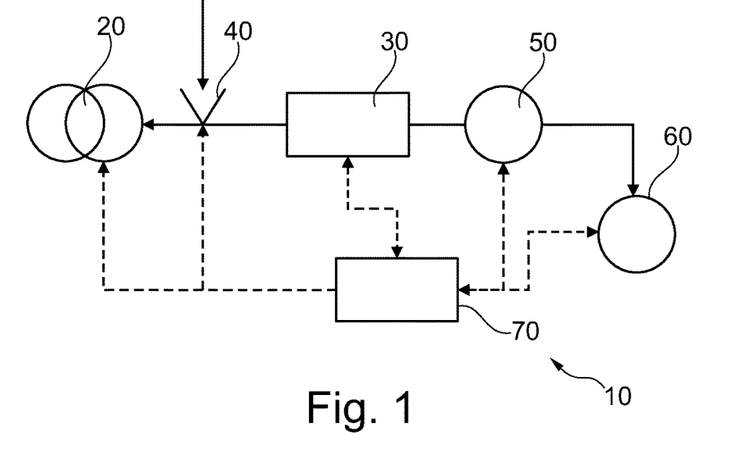
FIG. 1 is a simplified block diagram showing a sample separation system in accordance with exemplary embodiments of the invention, for example, used in high performance liquid chromatography (HPLC).

Referring now in greater detail to the drawings, FIG. 1 depicts a general schematic of a liquid separation system 10 as a sample separation system in accordance with an embodiment of the present invention. A pump 20 receives a mobile phase from a solvent supply, typically via a degasser, which degases and thus reduces the amount of dissolved gases in the mobile phase. The pump 20—as a mobile phase drive—drives the mobile phase through a separating device 30 (such as a chromatographic separation column) comprising a stationary phase. A sampling unit 40 can be provided between the pump 20 and the separating device 30 in order to subject or add (often referred to as sample introduction) a fluidic sample into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

The detector 50 is illustrated in FIG. 1 in a schematic way only. However, the below described figures will provide details as to how such a detector, and particularly an adjustable aperture thereof, can be configured according to exemplary embodiments.

While the mobile phase can be comprised of one solvent only, it may also be mixed from plural solvents. Such mixing may be a low pressure mixing and provided upstream of the pump 20, so that the pump 20 already receives and pumps the mixed solvents as the mobile phase. Alternatively, the pump 20 may be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, may be coupled (as indicated by the dotted arrows) to one or more of the components in the liquid separation system 10 in order to receive information and/or control operation. For example, the data processing unit 70 may control operation of the pump 20 (for example setting control parameters) and receive therefrom information regarding the actual working conditions (such as output pressure, flow rate, etc. at an outlet of the pump 20). The data processing unit 70 may further control operation of the sampling unit 40 (for example controlling sample injection or synchronization of sample injection with operating conditions of the pump 20). The separating device 30 may also be controlled by the data processing unit 70 (for example selecting a specific flow path or column, setting operation temperature, etc.), and send—in return—information (for example operating conditions) to the data processing unit 70. Accordingly, the detector 50 may be controlled by the data processing unit 70 (for example with respect to spectral or wavelength settings, setting time constants, start/stop data acquisition), and send information (for example about the detected sample compounds) to the data processing unit 70. The data processing unit 70 may also control operation of the fractionating unit 60 (for example in conjunction with data received from the detector 50) and provide data back.

Figure 2:
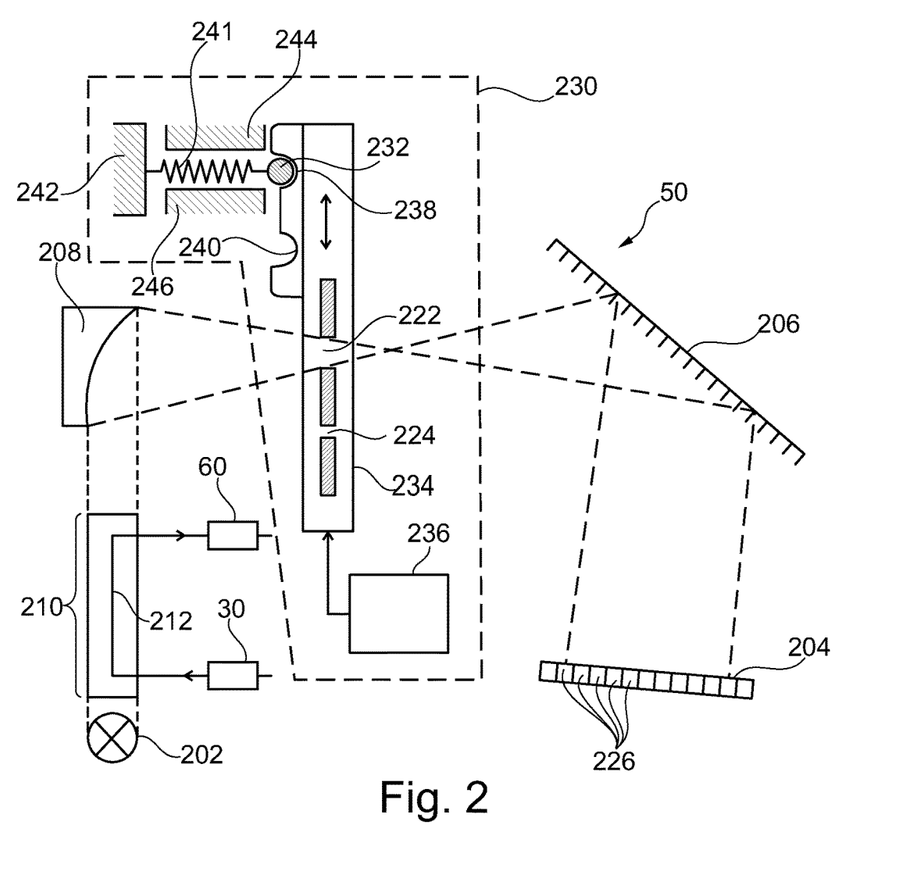
FIG. 2 a simplified block diagram showing an optical system with a flow cell used in conjunction with a sample detection apparatus according to an exemplary embodiment of the invention.

FIG. 2 shows a detailed view of the detector 50 of FIG. 1 according to an exemplary embodiment of the invention which can also be denoted as an ultraviolet radiation detecting apparatus. FIG. 2 shows a flow cell 210 which includes a capillary 212 conducting the separated fluidic sample through the flow cell 210. The flow cell 210 is located downstream of the separating device 30 so that the individual fractions of the fluidic samples are already separated at the position of the flow cell 210. The flow cell 210 is furthermore arranged upstream of the fractionating unit 60.

An UV light source 202 such as a Xenon lamp is configured for generating primary ultraviolet radiation which is directed onto the fluidic sample while flowing through the conduit 212 of the flow cell 210. In accordance with the physical properties of the fractions of the fluidic sample, the secondary UV light which is directed towards a deflection mirror 208 is a finger print of the fluidic sample. The deflection mirror 208 deflects the UV light and guides the latter through a first aperture hole 222 (or alternatively through a second aperture hole 224) of an aperture device 230 according to an exemplary embodiment of the invention.

After having passed the first aperture hole 222, the UV light falls onto a grating 206. At grating 206, the secondary UV light is split into the various spectral components, i.e. is separated into the different wavelength portions. The wavelength split secondary UV light is then directed towards a linear array of photo cells 226 of a linear photo cell array 204.

The adjustable aperture device 230 according to an exemplary embodiment of the invention comprises a sphere 232 as a position adjustment body. Any of the selectable first and second aperture holes 222, 224 can be selected and can therefore be driven into the UV beam path by moving an aperture body 234 (in which the first and second aperture holes 222, 224 are integrally formed) linearly by a linear drive unit 236. Therefore, depending on the motion of the drive unit 236, the aperture body 234 will be moved upwardly or downwardly as indicated by a double arrow in FIG. 2. Therefore, the sphere 232 will be locked in one of two engagement indentations 238, 240 formed along an edge of the aperture body 234. In the shown embodiment, the sphere 232 is locked within engagement indentation 238. The sphere 232 is biased against the edge of the aperture body 234 by a spring 241 which is mounted between a support wall 242 and the sphere 232. A lateral motion of the sphere 232 is limited by a first guide plate 244 and an opposing second guide plate 246. Therefore, the motion direction of the sphere 232 is limited to a horizontal linear direction.

Therefore, by moving the aperture body 234 by the drive unit 236, one of the first and second aperture holes 222, 224 may be aligned in the active optical path. This is in the present embodiment the first aperture hole 222 through which the UV beam is passed. While drive unit 236 provides the mechanical energy for driving the aperture body 234, the position adjustment is performed by the combination of components 232, 238, 240, 241, 242, 244, 246.

While the embodiment of FIG. 2 relies on a linear motion of a plate-shaped aperture body 234, another exemplary embodiment of an adjustable aperture device 300 for an the detector 50 (e.g., UV detecting apparatus) will be described in the following in which an adjustment of a selected aperture hole is performed based on a rotational switching.

Figure 3:
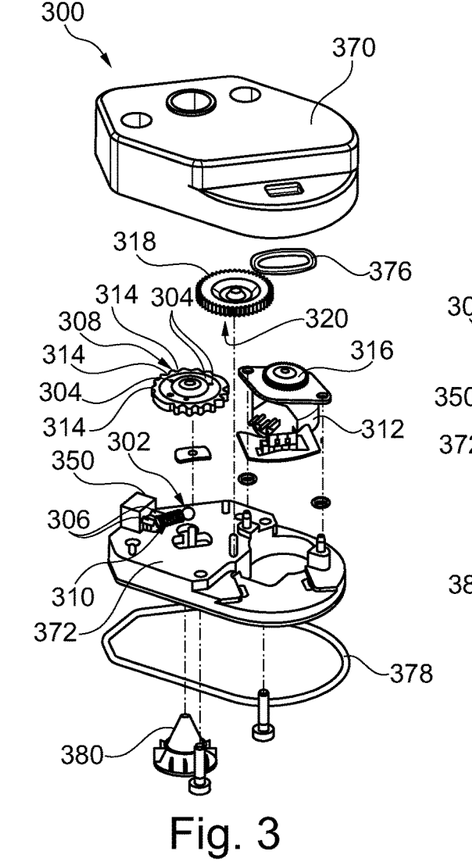
FIG. 3 is an exploded view of individual parts of an adjustable aperture device according to an exemplary embodiment of the invention.
Figure 4:
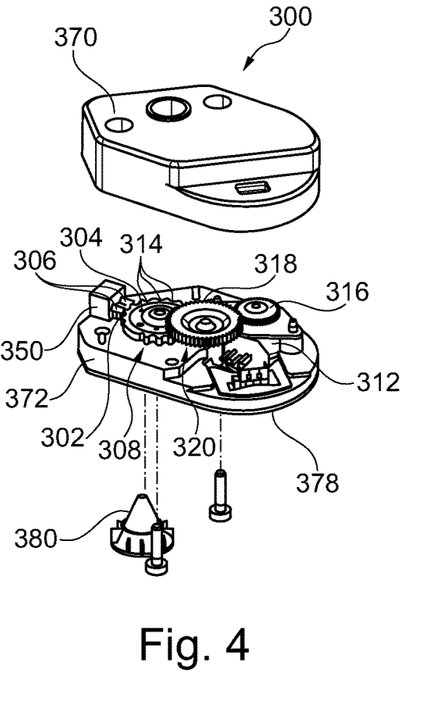
FIG. 4 is a partially exploded view of subassemblies assembled from the individual parts of FIG. 3 of the adjustable aperture device according to the exemplary embodiment of the invention.

FIG. 3 shows the adjustable aperture device 300 in an exploded view. FIG. 4 shows a part of the components of FIG. 3 in a partially assembled state.

Figure 5:
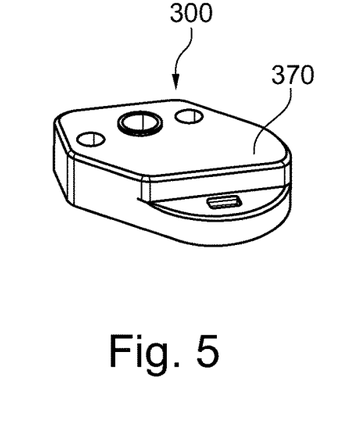
FIG. 5 is a three-dimensional top perspective view of the adjustable aperture device of FIG. 3 in an assembled state.
Figure 6:
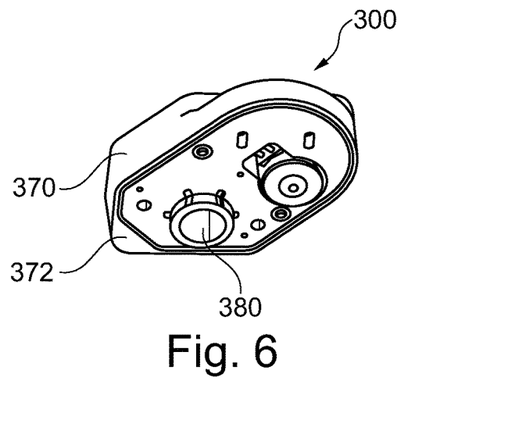
FIG. 6 is a three-dimensional bottom perspective view of the adjustable aperture device of FIG. 3 in an assembled state.

FIG. 5 shows the adjustable aperture device 300 in a completely assembled state in a top view, whereas FIG. 6 shows the same assembled adjustable aperture device 300 in a bottom view. The position adjustment mechanism can be derived particularly well from the detail views of FIG. 7 and FIG. 8.

The adjustable aperture device 300 has a position adjustment body, such as position adjustment sphere 302, which is configured for adjusting a position of a respectively selected aperture hole 304 which can be selected and activated among a number of selectable aperture holes 304, which may have different sizes and/or different shapes. The various aperture holes 304 are embodied as through holes formed through an aperture body, such as aperture wheel 308. When one of the aperture holes 304 is selected, this selected aperture hole 304 is aligned so that it can be traversed by the UV beam, as shown for the first aperture hole 222 in FIG. 2.

Figure 7:
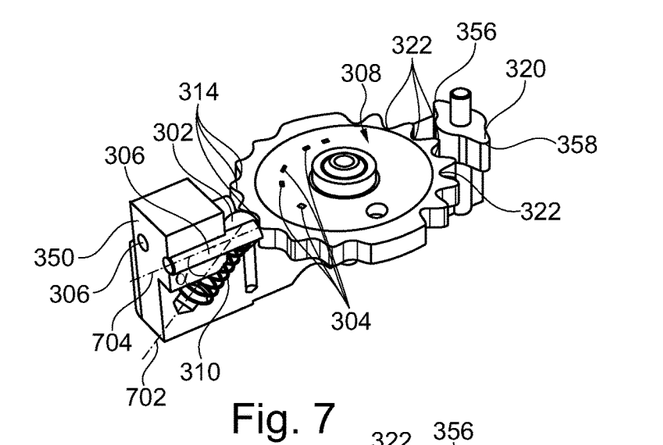
FIG. 7 is a first three-dimensional top perspective view of components of the adjustable aperture device of FIG. 3 which contribute to the aperture adjustment.

As can be best seen in FIG. 7, a guide unit is provided, such as two cylindrical guide pins 306 mounted in parallel to one another on a support body 350. The position adjustment sphere 302 is mounted between the guide pins 306 so that it can only move in one linear direction, i.e. along the cylinder axes of guide pins 306. At each position along an enabled motion trajectory, the position adjustment sphere 302 contacts exactly two points of the guide pins 306.

A pre-loading element, such as pre-loading spring 310, and the guide pins 306 are configured for applying a guiding pre-loading force to the position adjustment sphere 302 for forcing the position adjustment sphere 302 to apply an abutting force to the aperture wheel 308, which abutting force is oriented towards a rotation axis of the aperture wheel 308. The pre-loading spring 310 is provided for pre-loading the position adjustment sphere 302 towards the edge of the aperture wheel 308. The direction and amplitude of the pre-loading force may be adjusted by correspondingly designing the properties of the pre-loading spring 310, which may be a helical spring, for example.

The aperture wheel 308 is provided with the aperture holes 304 which are formed as through holes in the aperture wheel 308. Furthermore, a part of a circumferential edge of the toothed aperture wheel 308 has a number of engagement sections 314, e.g., formed as indentations between adjacent teeth. The engagement sections 314 and the position adjustment sphere 302 are matched so that the position adjustment sphere 302 can be engaged in a mechanically stable way in each of the engagement sections 314.

FIG. 7 shows a scenario in which the position adjustment sphere 302 is engaged in one of the engagement sections 314. It will be appreciated by a skilled person that the selection of a specific engagement section 314 in which the position adjustment sphere 302 is presently engaged corresponds unambiguously with one of the aperture holes 304 being selected or actuated.

A drive unit, such as stepper motor 312, is provided for driving the aperture wheel 308 via a gear mechanism which will be described below in more detail. In other words, the stepper motor 312 provides the mechanical energy by which the aperture wheel 308 is rotated. Thus, the rotation energy is provided by the stepper motor 312.

Figure 8:
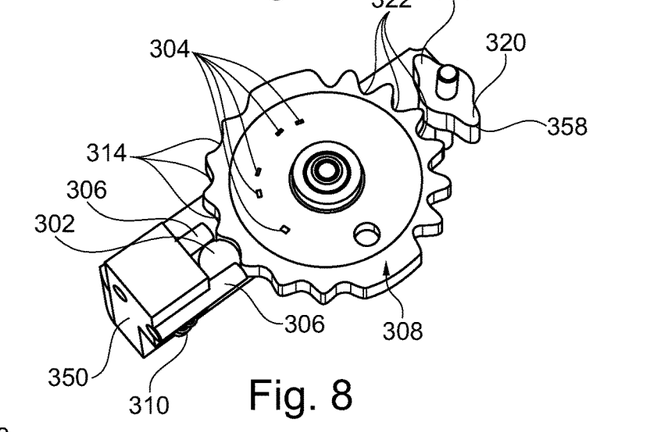
FIG. 8 is a second three-dimensional top perspective view of components of the adjustable aperture device of FIG. 3 which contribute to the aperture adjustment.

The above mentioned gear mechanism comprises, as can be best seen in FIG. 3 and FIG. 4, a toothed first gear wheel 316 mounted on and being driven by the stepper motor 312 and a toothed second gear wheel 318 which cooperates engagingly with the first gear wheel 316. Additionally, as can be best seen in FIG. 7 and FIG. 8 (in which the second gear wheel 318 is omitted for illustrative purposes), a bottom surface of the second gear wheel 318 has a camshaft 320 (which may also be denoted as switch-cams) configured for engaging with energy transfer engagement sections 322 arranged along a circumferential part of the aperture wheel 308. In other words, the aperture wheel 308 has a first circumferential part along which the engagement sections 314 are formed. It has a second circumferential part along which the energy transfer engagement sections 322 are formed. By equipping the camshaft 320 with only two protrusions 356, 358 or cams being configured for operating the aperture wheel 308 by engaging the respective energy transfer engagement sections 322, it can be ensured that the camshaft 320 is decoupled from the aperture wheel 308 upon completion of an adjustment procedure of the aperture device 300. However, in other embodiments, the number of protrusions 356, 358 or cams may also be different from two (for instance may be one, three, four, or larger than four). FIG. 7 and FIG. 8 show part of a shift wheel in the form of the camshaft 320 and of a switch wheel in form of the aperture wheel 308. Between the two parallel guide pins 306, a prismatic groove is formed for guiding the position adjustment sphere 302.

As can be taken best from FIG. 7, the pre-loading spring 310 applies a pre-loading force to the position adjustment sphere 302 along a pre-loading force direction 702 which is inclined by an inclination angle α relative to a guide direction 704 along which the guide pins 306 enable motion of the position adjustment sphere 302. For instance, the inclination angle α may be 45°. More generally, the inclination angle α may for instance be in a range between 20° and 70°.

FIG. 3 to FIG. 6 show further components of the adjustable aperture device. Particularly, a cover 370 which may be made of aluminum material may be mounted on the assembled movable components for protection purposes. The various components may be mounted on a support body 372 which may be made of aluminum material. Rings 376, 378 may be foreseen as well (these may be Silicone Rubber sealing-rings, not shown as normal "O-Rings" but in the unnatural assembled shape). A light trap cone 380 may be mounted on the adjustable aperture device 300 as well for avoiding undesired reflections of light to further improve the accuracy of the detection. With the adjustable aperture device 300 it is possible to obtain a position accuracy of better than 1 µm. Prototypes have still fulfilled all requirements after one million switches.

Hence, the adjustable aperture device 300 shown in FIG. 3 to FIG. 8 is a positioning system which aligns two angularly arranged prismatic guides in form of engagement sections 314 by means of the position adjustment sphere 302 biased by a spring force of the helical spring 310 and being laterally guided by guide pins 306. By aligning several prismatic structures radially on a disk, see aperture wheel 308, different positions can be reproducibly adjusted (switch wheel concept). The pre-loading force has the effect that on the one hand the clearance of the switch wheel is always equilibrated in the same direction, and that on the other hand external influences such as thermal expansion, sphere tolerances or wear do not have an influence on the positioning accuracy in view of the symmetric arrangement of the mechanical components. In order to prevent deterioration of the positioning, the switch drive (switch wheel), see first and second gear wheels 316, 318, is out of engagement at the point of time of their positioning. Hence, a bottom side of the second gear wheel 318 comprises the above-mentioned opposing cams (see camshaft 320) which allow for a free locking of the position adjustment sphere 302.

Figure 9:
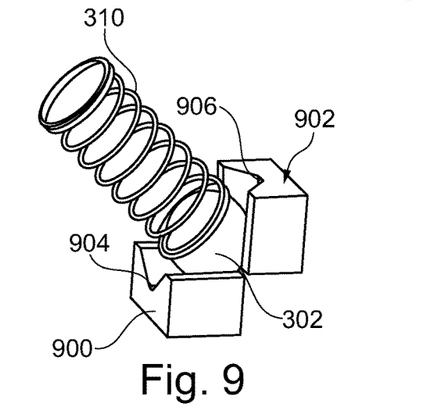
FIG. 9 is a three-dimensional perspective view showing a detail of FIG. 7 and FIG. 8.

As can be taken from FIG. 9, the engagement section 902 may be configured as having a prismatic groove 906. Accordingly, the guide pins 900 may also be embodied by a prismatic groove 904. The position adjustment sphere 302 hence contacts the engagement sections 902 as well as the guide pins 900 each at correspondingly defined points only.

Figure 10:
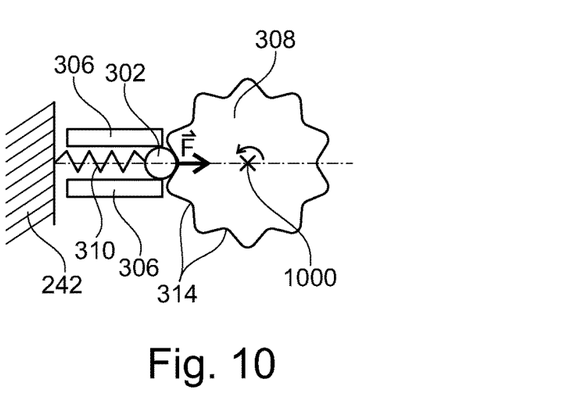
FIG. 10 is a plan view showing a relationship between a direction of an abutting force applied by a position adjustment sphere against an aperture body and a position of a rotation axis of the aperture body.

FIG. 10 illustrates a scenario in which the pre-loading spring 310 and the two parallel guide pins 306 are arranged relative to one another and relative to the sphere 302 and to the aperture wheel 308 to apply a directionally well-defined pre-loading force F to the sphere 302 for forcing the latter to apply an abutting force F to the aperture wheel 308 which abutting force F is oriented towards a rotation axis 1000 of the aperture wheel 308. Particularly, the projection of the pre-loading force F or the resulting abutting force F on the main plane of the aperture wheel 308 (i.e. the paper plane of FIG. 10) is directed towards the penetration point of the rotation axis 1000 through the main plane. In this case, a particularly accurate positioning is enabled.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

While the disclosure references exemplary embodiments, it will be apparent to those skilled in the art that various changes and modifications may be made without departing from the spirit and scope of the present teachings. Therefore, it should be understood that the above embodiments are not limiting, but illustrative.

The invention claimed is:

1. An adjustable aperture device for an electromagnetic radiation detecting apparatus, the aperture device comprising:

a position adjustment body configured for adjusting a position of a selected aperture hole of a plurality of selectable aperture holes, wherein electromagnetic radiation is to propagate through the selected aperture hole;
   a guide unit configured for guiding the position adjustment body along a predefined guide direction, wherein the guide unit is configured for guiding the position adjustment body via exactly two contact points defining degrees of freedom according to which the position adjustment body is allowed to move;
   an aperture body defining the plurality of aperture holes and comprising a plurality of engagement sections configured for selectively receiving the position adjustment body from the guide unit, wherein the position adjustment body is engagable in a selectable one of the plurality of engagement sections to thereby select the selected aperture hole from the plurality of selectable aperture holes;
   a pre-loading element configured for pre-loading the position adjustment body towards the aperture body; and
   a drive unit configured for driving the aperture body to move so that the position adjustment body is engaged in a respective one of the plurality of engagement sections.

2. The aperture device according to claim 1, wherein the position adjustment body is a sphere.

3. The aperture device according to claim 1, wherein the position adjustment body comprises a cylinder with a cone or ball-tip or any orbiform.

4. The aperture device according to claim 1, wherein the guide unit comprises two cylindrical guide pins mounted in parallel to one another.

5. The aperture device according to claim 1, wherein the guide unit comprises one of a prismatic structure having planar or concave or convex shaped walls or a guide pin in combination with a guide plate.

6. The aperture device according to claim 1, wherein the pre-loading element comprises a spring.

7. The aperture device according to claim 1, wherein the pre-loading element comprises one of a magnetic force generating system, an electrostatic force generating system, an elastic rod, and a system using gravitational force.

8. The aperture device according to claim 1, wherein the plurality of aperture holes in the aperture body have different sizes or different shapes.

9. The aperture device according to claim 1, wherein the plurality of engagement sections comprise a plurality of indentations formed between adjacent teeth distributed along at least a part of a circumference of the aperture body, and
   wherein the aperture body is configured to be rotatable by the drive unit to engage the position adjustment body in one of the plurality of indentations.

10. The aperture device according to claim 1, wherein the aperture body is configured to be linearly translatable by the drive unit to thereby engage the position adjustment body in one of indentations, as the plurality of engagement sections, formed between adjacent teeth aligned along at least a part of an edge of the aperture body.

11. The aperture device according to claim 1, further comprising:
   a gear mechanism configured for transferring drive energy from the drive unit to the aperture body.

12. The aperture device according to claim 11, wherein the gear mechanism comprises a first toothed gear wheel mounted on the drive unit and a second toothed gear wheel cooperating engagingly with the first toothed gear wheel, wherein the second toothed gear wheel has a camshaft configured for engaging with one or more energy transfer engagement sections arranged along at least a part of a circumference of the aperture body.

13. The aperture device according to claim 12, wherein the camshaft is configured for being decoupled from the aperture body upon completion of an adjustment procedure of the aperture device.

14. The aperture device according to claim 1, wherein a position adjustment performed by the position adjustment body, the guide unit and the pre-loading element is functionally decoupled from a driving of the aperture body performed by the drive unit.

15. The aperture device according to claim 1, wherein the plurality of engagement sections are configured as prismatic grooves formed between correspondingly shaped protrusions along an edge of the aperture body.

16. The aperture device according to claim 1, wherein the pre-loading element is configured for applying a pre-loading force to the position adjustment body along a pre-loading force direction, which is inclined relative to a guide direction along which the guide unit enables motion of the position adjustment body.

17. The aperture device according to claim 1, wherein the pre-loading element and the guide unit are configured for applying a guided pre-loading force to the position adjustment body for forcing the position adjustment body to apply an abutting force oriented towards a rotation axis of the aperture body.

18. An electromagnetic radiation detecting apparatus for detecting electromagnetic radiation carrying information indicative of components of a fluidic sample separated by a sample separation system, the electromagnetic radiation detecting apparatus comprising:
   an electromagnetic radiation source configured for generating primary electromagnetic radiation and for directing the primary electromagnetic radiation onto the separated fluidic sample;
   an electromagnetic radiation detector configured for detecting secondary electromagnetic radiation resulting from interaction of the components of the fluidic sample with the primary electromagnetic radiation; and
   an adjustable aperture device arranged in an electromagnetic radiation path between the electromagnetic radiation source and the electromagnetic radiation detector, the adjustable aperture device comprising:
      a position adjustment body configured for adjusting a position of a selected aperture hole of a plurality of selectable aperture holes, the electromagnetic radiation propagating through the selected aperture hole;
      a guide unit configured for guiding the position adjustment body along a predefined guide direction, wherein the guide unit is configured for guiding the position adjustment body via exactly two contact points defining degrees of freedom according to which the position adjustment body is allowed to move;
      an aperture body defining the plurality of aperture holes and comprising a plurality of engagement sections configured for selectively receiving the position adjustment body from the guide unit, wherein the position adjustment body is engagable in a selectable one of the plurality of engagement sections to thereby select the selected aperture hole from the plurality of selectable aperture holes;
      a pre-loading element configured for pre-loading the position adjustment body towards the aperture body; and
      a drive unit configured for driving the aperture body to move so that the position adjustment body is engaged with a respective one of the plurality of engagement sections.

19. The electromagnetic radiation detecting apparatus according to claim 18, wherein the electromagnetic radiation source comprises one of a deuterium lamp, a xenon lamp, and a tungsten lamp; and
   the electromagnetic radiation detector comprises one of an optical light detector, and an ultraviolet radiation detector.

20. A sample separation system for separating components of a fluidic sample, the sample separation system comprising:
   a mobile phase drive configured for driving a mobile phase through the sample separation system;
   a separation element configured for separating the components of the fluidic sample in the mobile phase; and
   an electromagnetic radiation detecting apparatus according to claim 18 for detecting electromagnetic radiation carrying information indicative of the components of the fluidic sample.

* * * * *